United States Patent [19]
Goble et al.

[11] Patent Number: 5,904,704
[45] Date of Patent: *May 18, 1999

[54] SUTURE ANCHOR ASSEMBLY

[75] Inventors: E. Marlowe Goble; David P. Luman, both of Logan, Utah; Harold M. Martins, Newtown, Mass.

[73] Assignee: Mitek Surgical Products, Inc., Westwood, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/514,613

[22] Filed: Aug. 14, 1995

[51] Int. Cl.⁶ .................................................... A61B 17/04
[52] U.S. Cl. ............................................. 606/232; 606/73
[58] Field of Search ................................ 606/232, 73, 75, 606/104, 65, 72; 411/388, 389, 393, 402

[56] References Cited

U.S. PATENT DOCUMENTS

| | | | |
|---|---|---|---|
| 1,269,971 | 6/1918 | Smith | 411/393 |
| 2,855,609 | 10/1958 | Moore | 411/393 |
| 5,156,616 | 10/1992 | Meadows et al. | 606/232 |
| 5,370,662 | 12/1994 | Stone et al. | 606/232 |
| 5,411,506 | 5/1995 | Goble et al. | 606/104 |
| 5,411,523 | 5/1995 | Goble | 606/73 |
| 5,573,548 | 11/1996 | Nazre et al. | 606/232 |
| 5,643,320 | 7/1997 | Lower et al. | 606/232 |

*Primary Examiner*—Michael Buiz
*Assistant Examiner*—Daphna Shai
*Attorney, Agent, or Firm*—Pandiscio & Pandiscio

[57] ABSTRACT

A structure anchor assembly having a suture anchor, a suture attached to the suture anchor, and an inserter for deploying the suture anchor in bone whereby the suture will extend from, and be anchored to, the bone. The suture anchor has a drill portion, a thread portion and a suture attachment portion. The drill portion is disposed on a distal portion of the anchor and is adapted to penetrate the bone. The thread portion extends proximally from the drill portion along the remainder of the length of the anchor and is adapted to draw the anchor through the bone. A proximal portion terminates in a proximal end surface. The thread portion extends along the proximal portion and terminates adjacent to the proximal end surface. The proximal portion of the anchor is adapted to: (i) be received in a distal end of the inserter prior to insertion of the suture anchor into the target bone, and (ii) be in threaded engagement with bone, once the suture attachment portion is disposed in the proximal portion of the anchor and is adapted to permit a length of suture to be attached to the anchor.

15 Claims, 11 Drawing Sheets

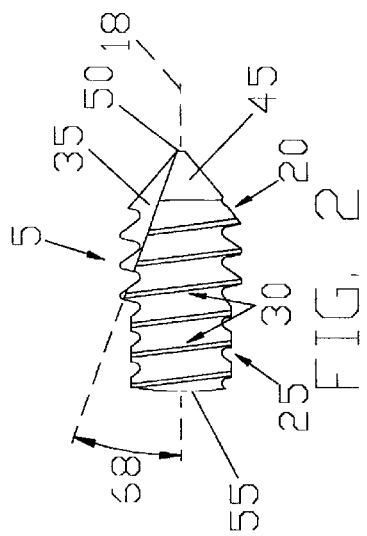
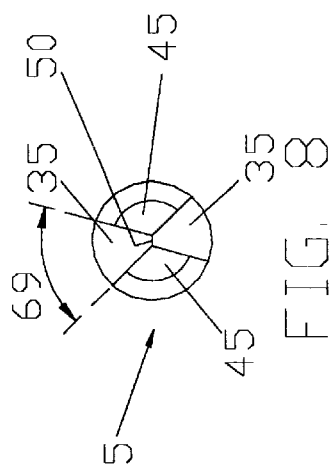
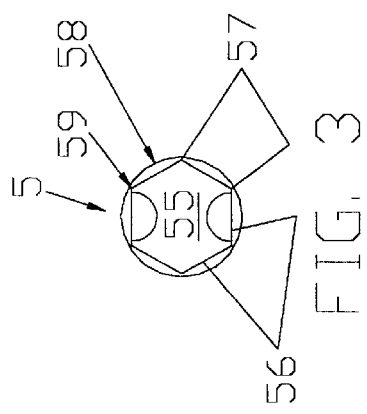
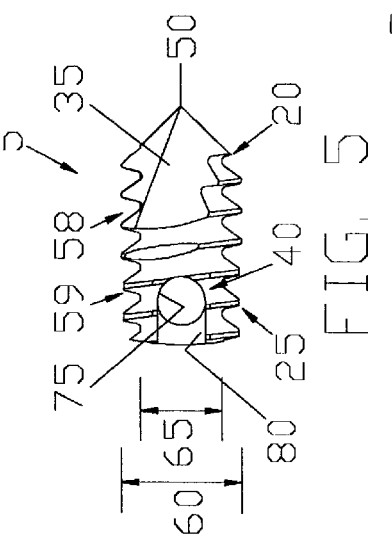
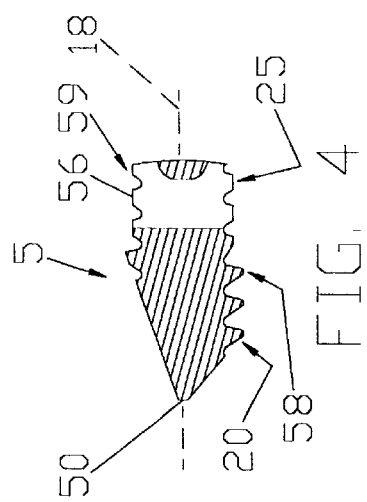
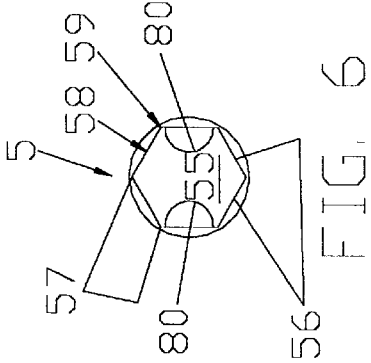

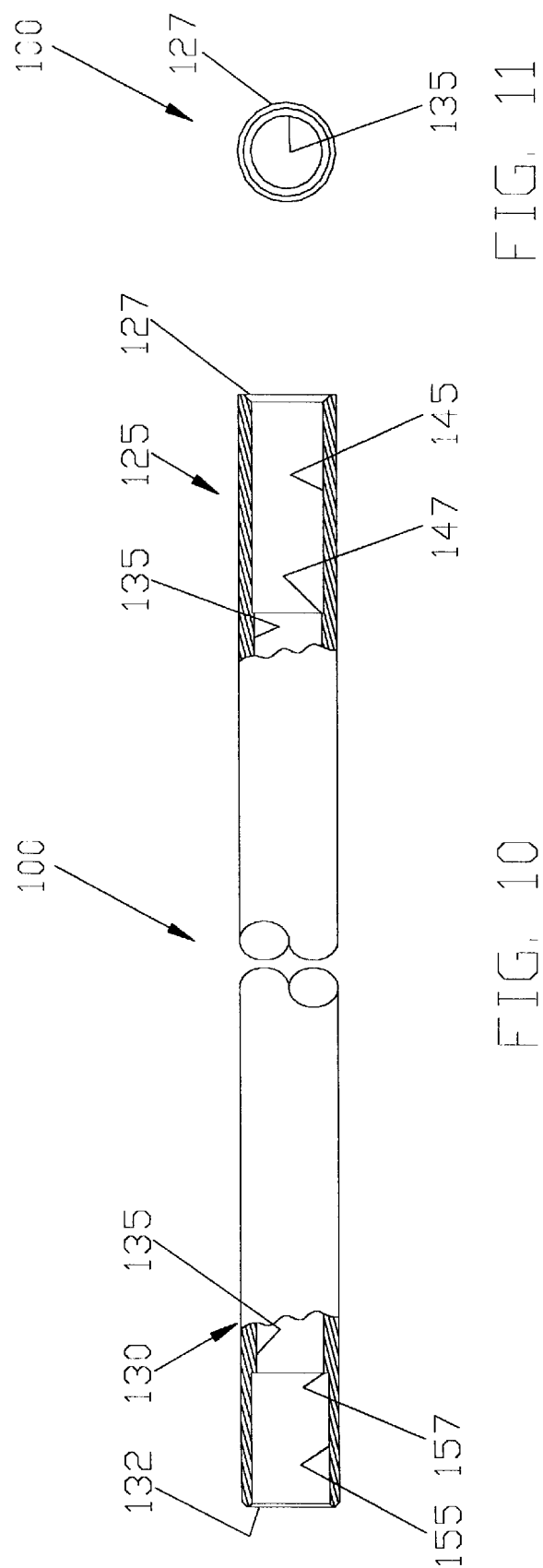

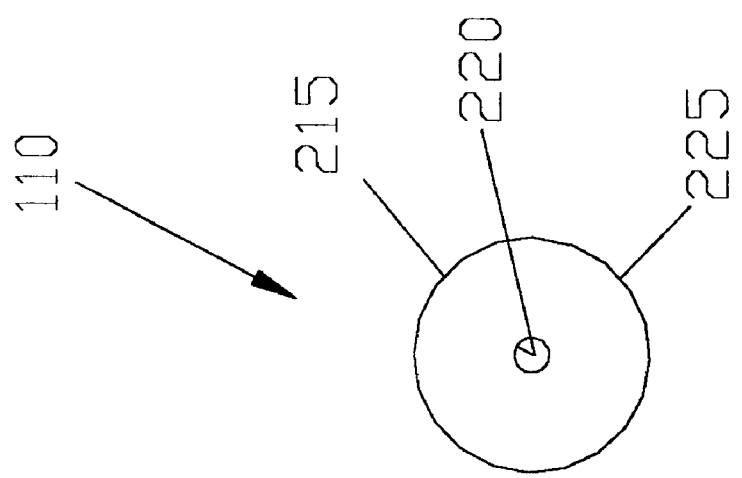
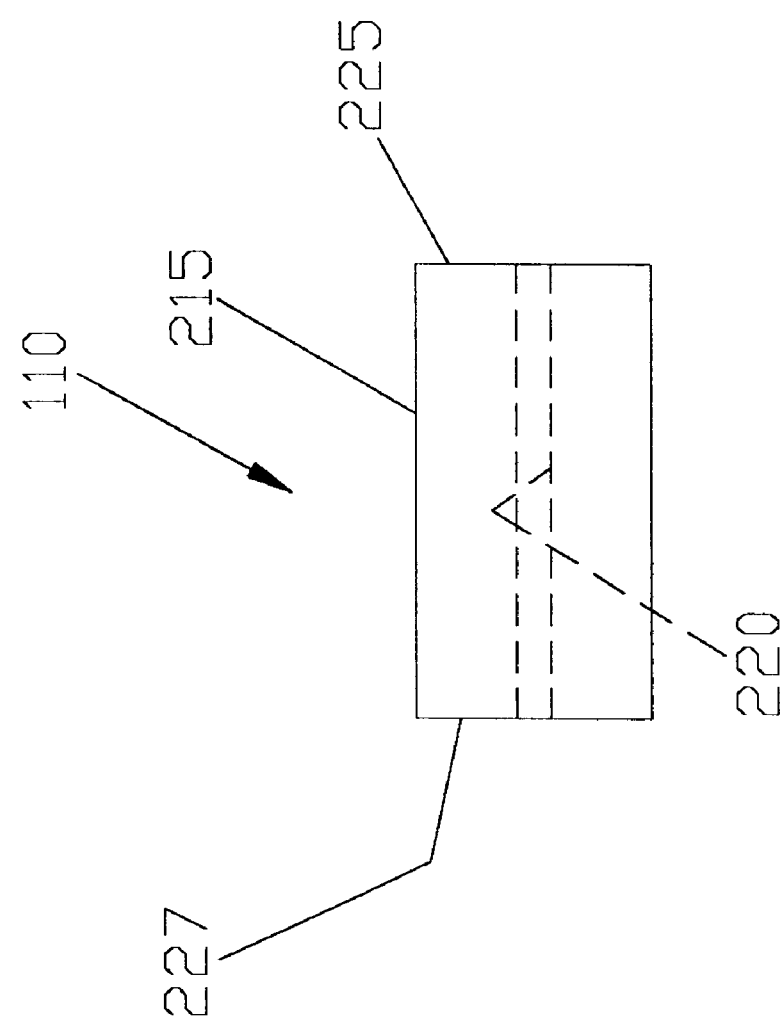

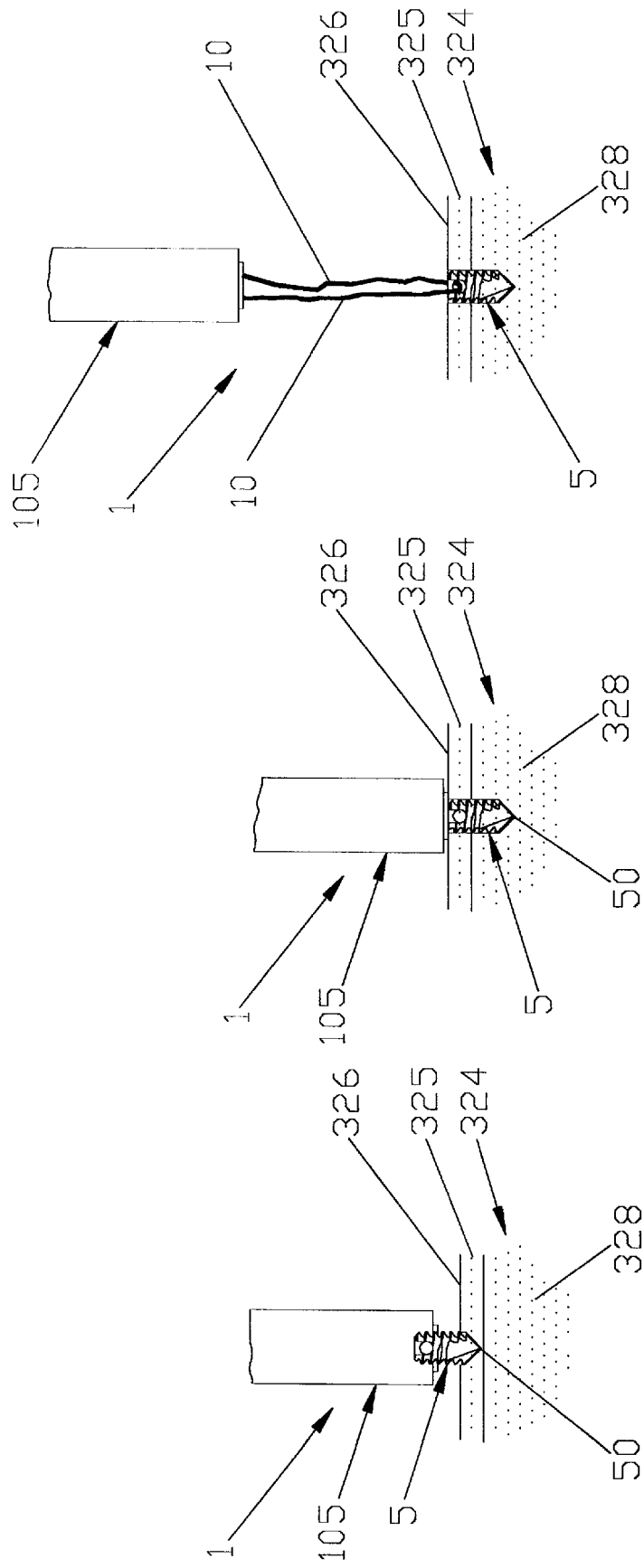

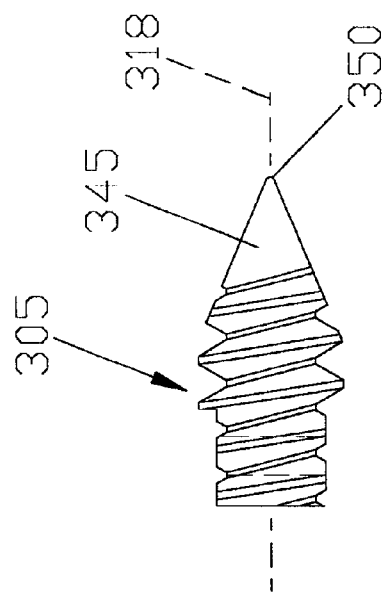
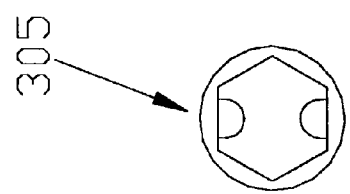
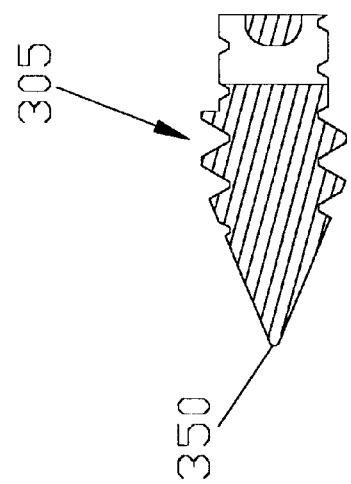
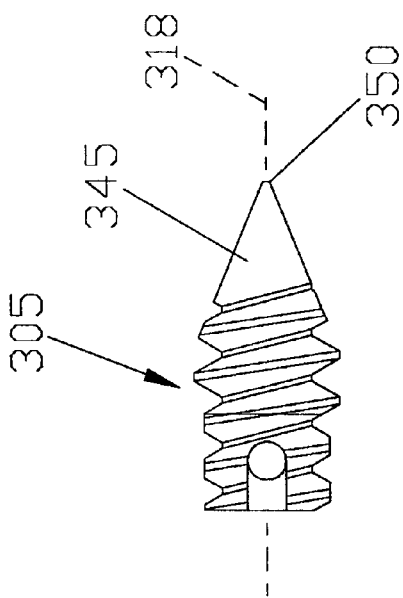
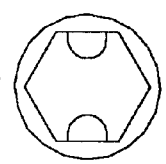
FIG. 25
FIG. 26
FIG. 27
FIG. 28
FIG. 29

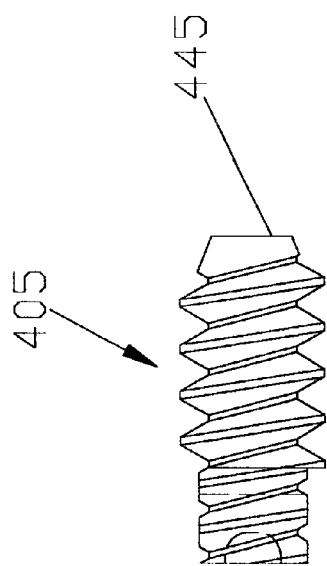
FIG. 30
FIG. 31
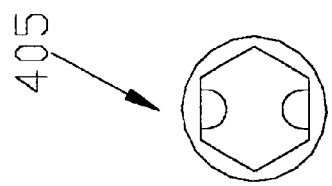
FIG. 32
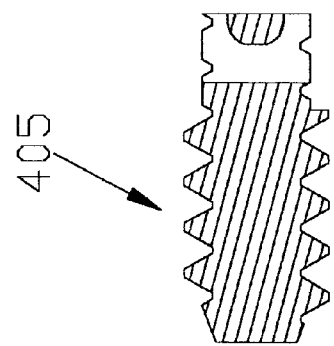
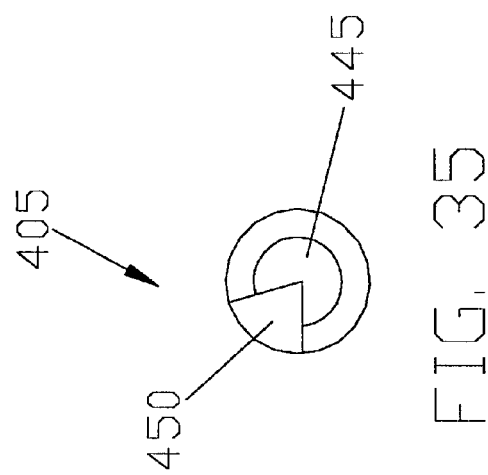
FIG. 35
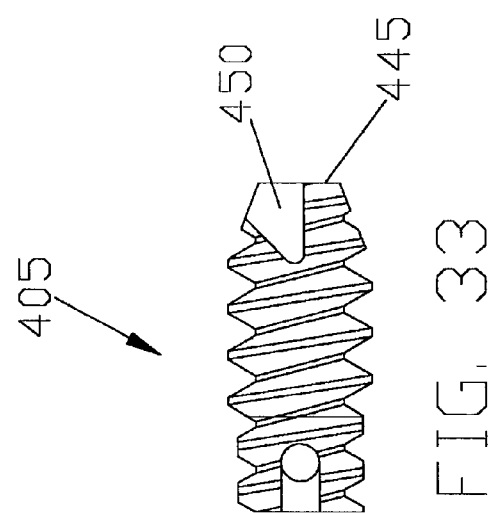
FIG. 33
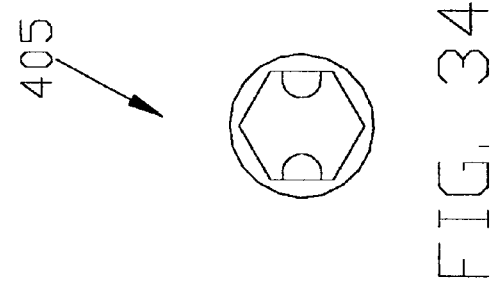
FIG. 34

SUTURE ANCHOR ASSEMBLY

FIELD OF THE INVENTION

The present invention relates generally to devices for attaching suture to bone, and more particularly to such devices that are self-tapping.

BACKGROUND OF THE INVENTION

A Self-tapping suture anchors are well known in the art. See, for example, U.S. Pat. No. 4,632,100, issued Dec. 30, 1986 to Goble et al., which discloses a cylindrical suture anchor having a drill portion formed at one end and flights of threads formed at the other end. A length of suture is fixedly attached to the suture anchor so as to extend therefrom. The suture anchor may be turned, and hence installed into a target bone, by means of a driver that matingly engages the anchor by means of a splined coupling, with the free end of the suture being stored within the body of the driver. In practice, the drill end of the suture anchor is positioned against the target bone and then the suture anchor is turned by means of the driver. This causes the drill portion of the suture anchor to cut into the bone. As the drill portion of the suture anchor cuts into the bone, thus forming a hole therein, the suture anchor's threads engage the inner surface of the hole. The leading thread flights tap the hole so as to provide a seat for the following thread flights. Once the suture anchor has been seated, the driver is pulled back from the bone, with the stored suture paying out from the interior of the driver.

While suture anchors of the type taught by Goble et al. generally perform well, they are not completely satisfactory for all types of surgical procedures in which suture must be attached to bone. In particular, with the suture anchor of Goble et al., the suture is attached to the anchor by fastening the suture to a disc, which is then fixed in position within a blind hole formed in the proximal end of the anchor. Unfortunately, this arrangement can be cumbersome, particularly where the anchor is to be formed with a relatively small size. Furthermore, with the suture anchor of Goble et al., the splined coupling used to connect the driver to the anchor comprises a polygonally-shaped male portion on the driver and a corresponding polygonally-shaped female portion on the anchor. This construction can present a constraint, particularly where it is desired to form the anchor in a relatively small size. Moreover, when the anchor of Goble et al. is installed in a target bone in the manner taught in the patent, the suture anchor's thread often does not positively engage the cortical layer of that bone. This has sometimes led to less than adequate retention of the suture anchor in the bone, especially where relatively small size anchors have been used.

OBJECTS OF THE INVENTION

Accordingly, one object of the present invention is to provide a novel suture anchor and a novel suture anchor inserter for deploying that anchor in bone.

Another object of the present invention is to provide a novel suture anchor comprising drill means, thread means, and suture attachment means, all formed with a unitary construction.

And another object of the present invention is to provide a novel suture anchor having a non-circularly-shaped proximal portion which is adapted to be received by a corresponding non-circularly-shaped recess formed in the suture anchor inserter.

And another object of the present invention is to provide a novel suture anchor having a polygonally-shaped proximal portion which is adapted to be received by a corresponding polygonally-shaped recess formed in the suture anchor inserter.

Still another object of the present invention is to provide a novel suture anchor wherein flights of threads extend along at least a portion of the anchor, including the non-circularly-shaped proximal portion of the anchor.

Yet another object of the present invention is to provide a novel suture anchor which is adapted to engage both cancellous bone and cortical bone when the suture anchor is deployed in a bone.

A further object of the present invention is to provide a novel suture anchor assembly having a reduced manufacturing cost.

Still another object of the present invention is to provide a novel system comprising a suture anchor, a suture attached to the suture anchor, and an inserter for deploying the suture anchor in bone, whereby the suture will extend from, and be anchored to, the bone.

Yet another object of the present invention is to provide an improved method for anchoring suture in bone.

SUMMARY OF THE INVENTION

These and other objects of the present invention are achieved by the provision and use of a novel suture anchor assembly which comprises a novel suture anchor, a suture attached to the suture anchor, and a novel inserter for deploying the suture anchor in bone whereby the suture will extend from, and be anchored to, the bone.

The novel suture anchor generally comprises drill means, thread means and suture attachment means. The drill means are disposed on a distal portion of the anchor and are adapted to penetrate the bone when the drill means are pressed against the bone and the anchor is rotated about its longitudinal axis. The thread means extend along at least a portion of the length of the anchor and are adapted to draw the anchor through the bone when the anchor is rotated. The proximal portion of the anchor comprises a non-circularly-shaped cross-section that terminates in a proximal end surface. The thread means extend along the aforementioned proximal portion of the anchor (as well as along at least a portion of the anchor distal thereto) and terminate adjacent to the proximal end surface. The proximal portion of the anchor is adapted to: (i) be received in the distal end of the novel inserter prior to insertion of the suture anchor into the target bone, and (ii) be in threaded engagement with cortical bone or cortical and/or cancellous bone once the suture anchor has been fully installed in the target bone. The suture attachment means are disposed in the proximal portion of the anchor and are adapted to permit a length of suture to be attached to the anchor.

In a preferred embodiment, the drill means comprise a pointed distal end surface disposed on a distal portion of the anchor, and at least one cutting flute that extends proximally from the distal end surface. The thread means comprise a single, continuous thread that extends from the anchor's distal end surface to the anchor's proximal end surface. The proximal portion of the anchor may comprise either a non-circular cross-section or a polygonally-shaped cross-section, with a hexagonal cross-section being preferred. The suture attachment means comprise a bore passing completely through the proximal portion of the anchor, and a pair of channels extending between the two ends of the bore and the proximal end surface of the anchor. The channels are adapted to receive a portion of a length of suture so as to: (i) permit the suture anchor to be mounted on the distal end of its associated inserter while a length of suture is attached to the anchor, (ii) prevent the thread on the proximal portion of the anchor from cutting the suture during insertion of the suture anchor into the target bone, and (iii) allow for sliding movement of the suture relative to the proximal portion of the anchor once the suture anchor has been installed in the target bone.

The foregoing suture anchor is intended to be installed in a target bone using the novel inserter of the present invention. The novel inserter comprises a tubular shaft having a tubular shaft tip. The tubular shaft tip comprises a recess extending proximally into its distal end. The recess is sized and shaped so as to matingly receive the proximal portion of the suture anchor, whereby the suture anchor can be rotated about its longitudinal axis using the inserter. The tubular shaft further comprises means for controlling and storing one or more lengths of suture emanating from the proximal portion of the anchor.

In an alternative form of the invention, the suture anchor may omit the drill means from its distal end. In this case the inserter is used to install the suture anchor into a hole which is pre-drilled into the target bone.

BRIEF DESCRIPTION OF THE DRAWINGS

These and other objects, features and advantages of the present invention will be more fully disclosed in, or rendered obvious by, the following detailed description of the preferred embodiments of the invention, which are to be considered together with the accompanying drawings wherein like numbers refer to like parts, and further wherein:

FIG. 2 is a side view of the suture anchor shown in FIG. 1, with the suture anchor having been rotated 90° about its longitudinal axis from the position shown in FIG. 1;

FIG. 3 is a rear end view of the suture anchor shown in FIG. 2;

FIG. 4 is a cross-sectional view of the suture anchor shown in FIG. 3;

FIG. 5 is another side view of the suture anchor shown in FIG. 2, with the suture anchor having been rotated 90° clockwise about its longitudinal axis from the position shown in FIG. 2;

FIG. 6 is a rear end view of the suture anchor shown in FIG. 5;

FIG. 7 is a partial, enlarged view of the continuous thread of the suture anchor shown in FIG. 5;

FIG. 8 is a front end view of the suture anchor shown in FIG. 2;

FIG. 10 is a side elevational view, partially broken away and partially in section, of the inserter's tubular shaft;

FIG. 11 is a front end view of the tubular shaft shown in FIG. 10;

FIG. 16 is a side view of the inserter's suture gripper;

FIG. 17 is a front end view of the suture gripper shown in FIG. 16;

FIG. 22 is a side view, partially in section, showing the suture anchor assembly after the pointed distal end surface of the suture anchor has penetrated the cortical layer of the target bone;

FIG. 23 is a side view, partially in section, showing the suture anchor assembly after the suture anchor has fully penetrated the target bone;

FIG. 24 is a side view, partially in section, showing the suture anchor installed in the target bone, with the inserter's tubular shaft tip withdrawn from the surface of the target bone and the suture paying out therefrom;

FIGS. 25–29 show an alternative embodiment of the novel suture anchor of the present invention; and FIGS. 30–35 show a further alternative embodiment of the novel suture anchor of the present invention.

DETAILED DESCRIPTION OF THE PREFERRED EMBODIMENTS

Figure 1:
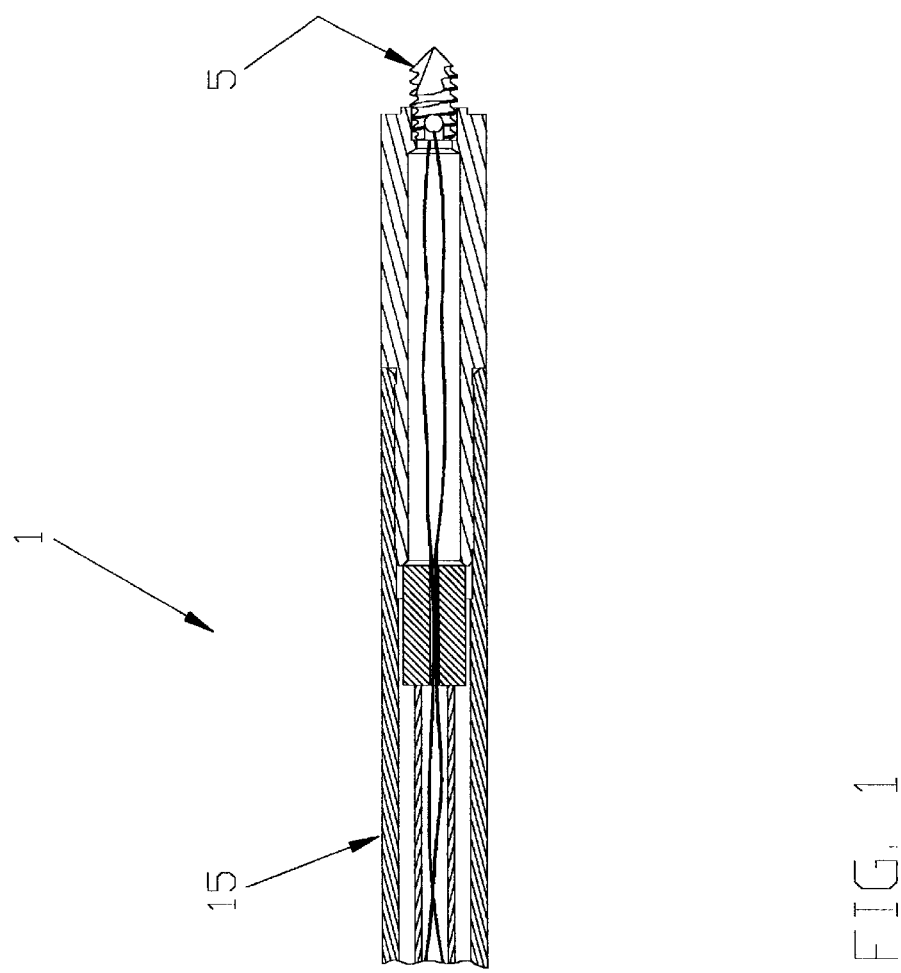
FIG. 1 is a side view, partially in cross-section, showing a suture anchor assembly formed in accordance with the present invention.

Referring first to FIG. 1, a suture anchor assembly 1 is shown which is formed in accordance with the present invention. Suture anchor assembly 1 generally comprises a suture anchor 5, a suture 10, and an inserter 15.

More particularly, and referring now to FIGS. 2–8, suture anchor 5 has a unitary construction and generally comprises a longitudinal axis 18, a distal portion 20, a proximal portion 25, a continuous thread 30, at least one cutting flute 35, and suture attachment means 40 (FIG. 5). Suture anchor 5 may be formed from any one of the various biocompatible or bioabsorbable materials well known in the art. For example, suture anchor 5 may be formed out of zirconia ceramics, stainless steel alloys, and poly-L-lactic acid polymers, among other materials. In one preferred embodiment, suture anchor 5 is formed from a blank of surgical grade titanium alloy.

The suture anchor's distal portion 20 includes a distal end surface 45 that terminates in a distal point 50. In the preferred embodiment, distal portion 20 comprises a generally cylindrical shape having a generally conical front tip. Of course, it will be understood that distal portion 20 may also comprise other shapes, such as a cone or polygon, without departing from the scope of the present invention. In a preferred embodiment, distal end surface 45 forms an approximately 90° included angle about distal point 50. Alternatively, other included angles may also be employed with favorable results.

Proximal portion 25 includes a proximal end surface 55 (FIGS. 2, 3 and 6) that is spaced away from distal portion 20. In a preferred embodiment, proximal portion 25 may have a generally polygonal cross-section. More particularly, proximal portion 25 may comprise a multi-faceted profile that includes a plurality of flat sides 56 separated by a plurality of corners 57 (FIGS. 3 and 6). For example, in one preferred embodiment, proximal portion 25 comprises a hexagonal cross-section. Of course, it will be understood that various other multi-faceted or generally non-circular cross-sections may also be used without departing from the scope of the present invention.

As seen in FIGS. 2, 4 and 5, continuous thread 30 extends across at least a portion of the anchor's distal portion 20 and across at least a portion of the anchor's proximal portion 25. More particularly, in the preferred embodiment, thread 30 comprises a first portion 58 that extends along distal portion 20 and a second portion 59 that extends along proximal portion 25 (FIGS. 5 and 6). First portion 58 and second portion 59 comprise: (i) a major diameter 60 and a minor diameter 65 (FIG. 5), (ii) an included thread angle 66 (FIG. 7) in the range of from about 5° to about 45°, with a preferred angle of about 36°, and (iii) a flank angle 67 (FIG. 7) in the range of from about 5° to about 45°, with a preferred angle of about 13°. On account of the polygonal cross-section of the anchor's proximal portion 25, however, the second portion 59 of thread 30 is retained principally across corners 57 of proximal portion 25, as seen in FIGS. 5 and 6. Between corners 57, second portion 59 of thread 30 is flattened so as to form each flat side 56 of proximal portion 25 (FIGS. 3 and 4). As a result of this construction, the proximal portion 25 of suture anchor 5 may be formed with a polygonal cross-section so as to be matingly received by inserter 15, yet with continuous thread 30 extending along the complete length of proximal portion 25 so as to provide the suture anchor with greater holding power when deployed in bone, as will hereinafter be described in further detail.

Looking next at FIGS. 2, 4, 5 and 8, at least one cutting flute 35 extends proximally from a portion of distal end surface 45, along a substantial portion of the length of thread 30. In a preferred embodiment, two cutting flutes 35 are provided (FIG. 8). Preferably, each cutting flute 35 extends along only the distal portion 20 of anchor 5 and does not extend into proximal portion 25 of anchor 5. Each flute 35 is sized and shaped so as to aggressively remove enough bone during each revolution of anchor 5 to allow each flight of thread 30 to advance forward into the target bone. In this respect it will be understood that the rate at which anchor 5 will advance into the target bone with each revolution will be determined by the pitch of its thread 30.

In a preferred embodiment, each flute 35 forms an angle 68 (FIG. 2) with the anchor's longitudinal axis 18 in the range of from about 15° to about 25°, with a preferred angle of about 20°. Each flute 35 also forms transverse included angle 69 (FIG. 8) on anchor 5 in the range of from about 50° to about 70°, with a preferred angle of about 60°. Of course, it will be understood that the values chosen for these angles may vary according to the selected flute length and other factors well known in the art.

As best seen in FIGS. 5 and 6, suture attachment means 40 comprise a bore 75 which extends transversely through the anchor's proximal portion 25. Bore 75 is positioned so as to be centered on two diametrically-opposing flat sides 56 of proximal portion 25. A pair of surface channels 80 communicate with, and extend proximally from, the two ends of bore 75. Channels 80 open on the anchor's proximal end surface 55 and provide clearance for suture 10 to pass between (i) suture anchor 5 and the adjacent portions of inserter 15 when the suture anchor is installed in inserter 15, and (ii) suture anchor 5 and the adjacent bone after suture anchor 5 has been installed in the target bone. In particular, channels 80 are sized so that suture 10 can be safely seated in channels 80 so as to prevent thread 30 from accidentally damaging the suture during (i) initial seating of the suture anchor in the distal end of inserter 15, and (ii) subsequent insertion of the suture anchor into the target bone. In addition, bore 75 and channels 80 are sized so as to allow suture 10 to slide freely relative to suture anchor 5 once the suture anchor has been installed in the target bone.

Figure 9:
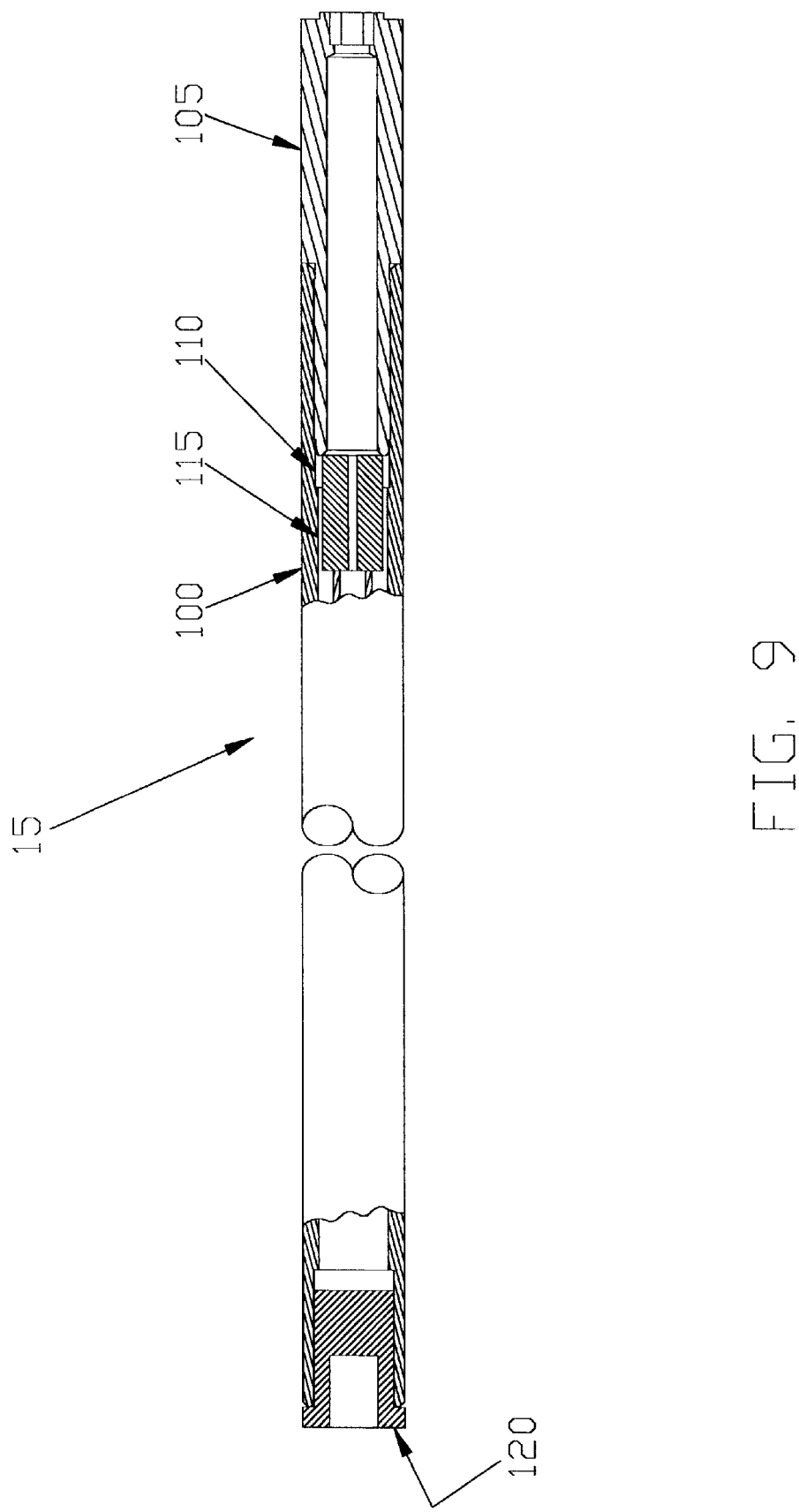
FIG. 9 is a side elevational view, partially broken away and partially in section, showing the inserter assembly shown in FIG. 1.

Suture anchor 5 is intended to be installed in a target bone by means of novel inserter 15. Referring now to FIG. 9, inserter 15 generally comprises a tubular shaft 100, a tubular shaft tip 105, a suture gripper 110, a suture sleeve 115, and a cap 120. In a preferred embodiment, inserter 15 is formed from one or more of the various biocompatible metal or polymer materials well known in the art.

More particularly, and now referring to FIGS. 10 and 11, tubular shaft 100 generally comprises a distal portion 125 terminating in a distal end surface 127, a proximal portion 130 terminating in a proximal end surface 132, and a central passageway 135. A distal counterbore 145 connects central passageway 135 with distal end surface 127. Distal counterbore 145 is adapted to receive tubular shaft tip 105, as will hereinafter be disclosed in further detail. An internal shoulder 147 is defined at the intersection of distal counterbore 145 with central passageway 135. A proximal counterbore 155 connects central passageway 135 with proximal end surface 132. Proximal counterbore 155 is adapted to receive cap 120, as will hereinafter be disclosed in further detail. An internal shoulder 157 is defined at the intersection of proximal counterbore 155 with central passageway 135.

Figure 14:
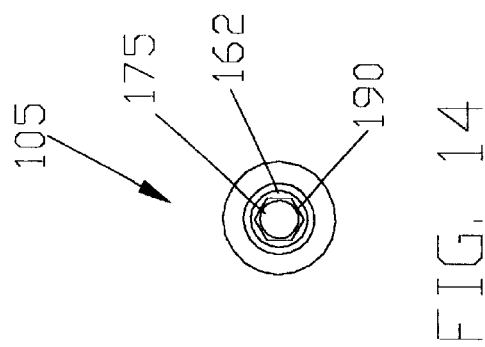
FIG. 14 is a front end view of the tubular shaft tip shown in FIG. 12.
Figure 15:
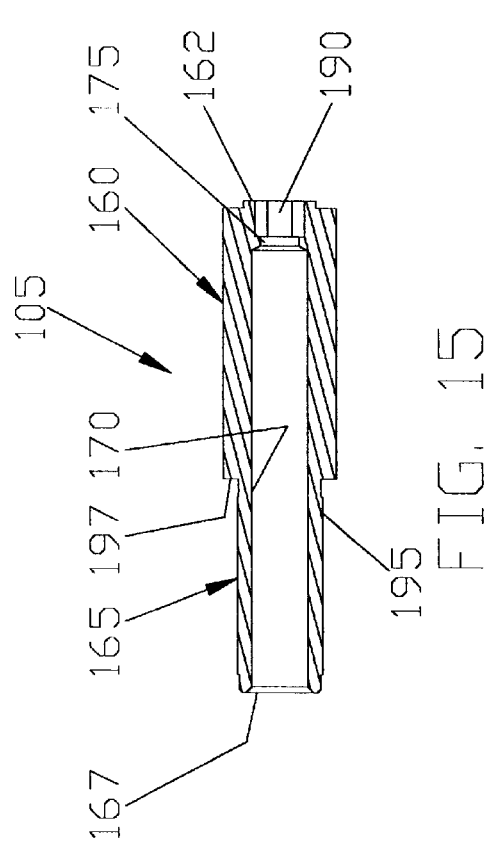
FIG. 15 is a side view, in cross-section, of the tubular shaft tip shown in FIG. 12, as taken along line 15–15 in FIG. 12.
Figure 12:
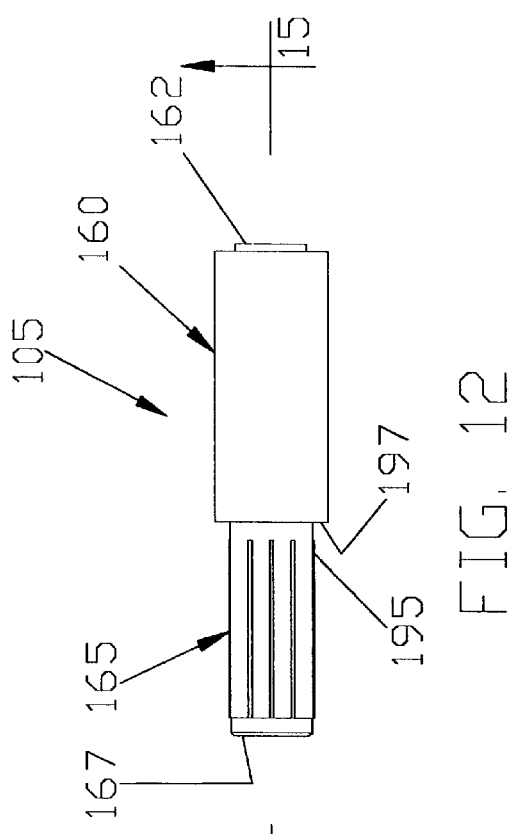
FIG. 12 is a side view of the inserter's tubular shaft tip.
Figure 13:
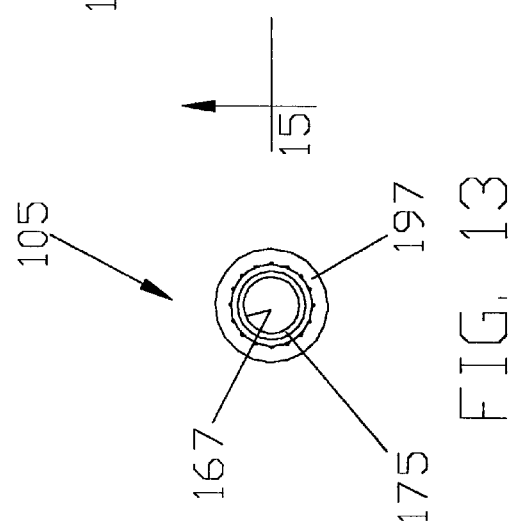
FIG. 13 is a rear end view of the tubular shaft tip shown in FIG. 12.

Referring now to FIGS. 12–15, tubular shaft tip 105 (FIG. 12) comprises a distal portion 160 terminating in a distal end surface 162, a cylindrical proximal portion 165 terminating in proximal end surface 167, and a central passageway 170 communicating between distal end surface 162 and proximal end surface 167. An annular projection 175 projects inwardly into central passageway 170 near the distal end of tubular shaft tip 105 (FIGS. 13, 14 and 15). The distal portion 190 (FIG. 15) of central passageway 170 (i.e., the portion of central passageway 170 extending between annular projection 175 and distal end surface 162) is provided with a polygonal or generally non-circular cross-sectional configuration. The particular cross-sectional configuration of distal portion 190 is sized and shaped so as to correspond to the cross-sectional shape of proximal portion 25 of anchor 5. As a result of this construction, the proximal portion of anchor 5 may be securely received in the central passageway's distal portion 190 prior to installation of anchor 5 in a target bone without causing damage to portions 58 and/or 59 of thread 30, as will hereinafter be disclosed in further detail. It is to be appreciated that when anchor 5 is mounted to tubular shaft tip 105 in the foregoing manner, annular projection 175 will act as a stop against which the suture anchor's proximal end surface 55 will rest. It is also to be appreciated that tubular shaft tip 105 and suture anchor 5 are sized such that when the suture anchor's proximal end surface 55 rests against the inserter's annular projection 175, the suture anchor's second thread portion 59 will remain completely outside of the inserter. As a result, the suture anchor's second thread portion 59 will be protected from damage during anchor turning. This is significant, since any damage to the suture anchor's second thread portion 59 can seriously impede proper anchor deployment.

Distal portion 160 may comprise either a frusto-conical or cylindrical shape. Cylindrical portion 165 of tubular shaft tip 105 comprises a distal end 195 which abuts a proximal end surface 197 of distal portion 160. Thus it will be seen that the shaft tip's cylindrical portion 165 projects proximally from the shaft tip's distal portion 160.

Referring next to FIGS. 16 and 17, suture gripper 110 comprises a cylindrical body 215 having an internal passageway 220 that communicates between end surfaces 225 and 227. Suture gripper 110 generally comprises an elastomeric material, and is sized and shaped to fit snugly within central passageway 135 of tubular shaft 100. Internal passageway 220 of suture gripper 110 is sized and shaped to snugly receive and control suture 10 when suture anchor 5 is fully assembled to inserter 15.

Figure 19:
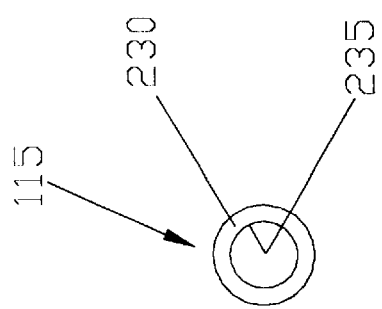
FIG. 19 is a front end view of the suture sleeve shown in FIG. 18.
Figure 18:
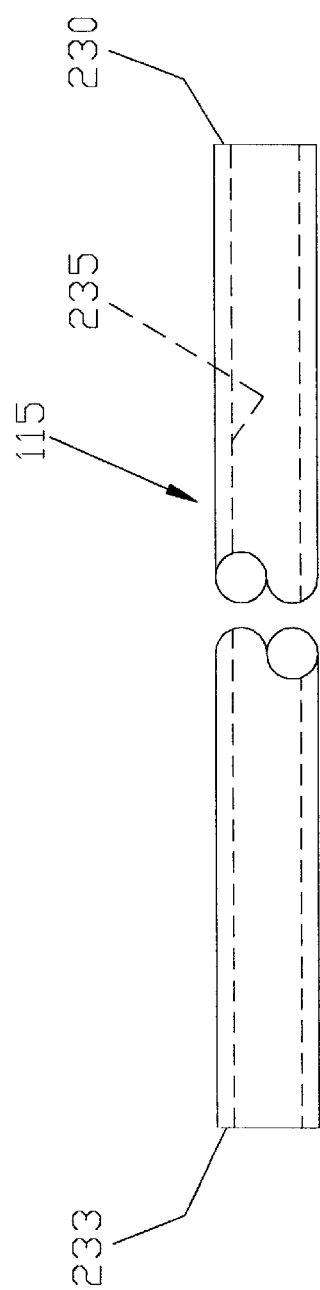
FIG. 18 is a side view of the inserter's suture sleeve.

Referring next to FIGS. 18 and 19, suture sleeve 115 comprises an elongated tube that is adapted to be slidingly received within tubular shaft 100. Suture sleeve 115 comprises a distal end surface 230, a proximal end surface 233, and a central passageway 235 extending between distal end surface 230 and proximal end surface 233. Suture sleeve 115 is adapted to loosely receive suture 10 when suture anchor 5 is fully assembled to inserter 15, as will hereinafter be disclosed in further detail.

Figure 21:
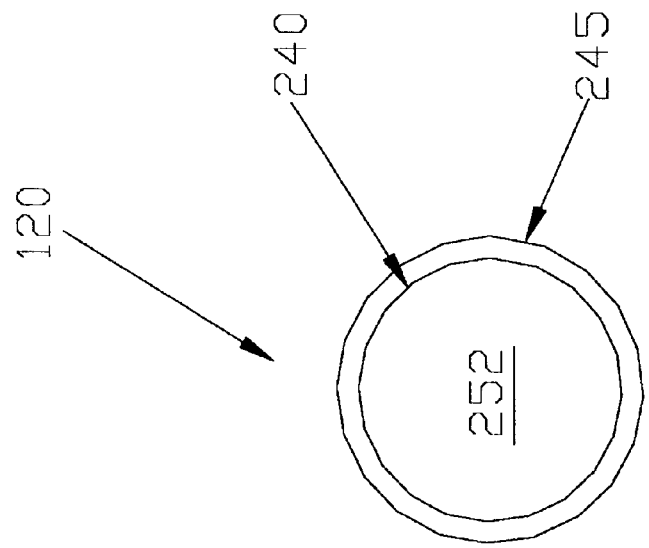
FIG. 21 is a front end view of the cap shown in FIG. 20.
Figure 20:
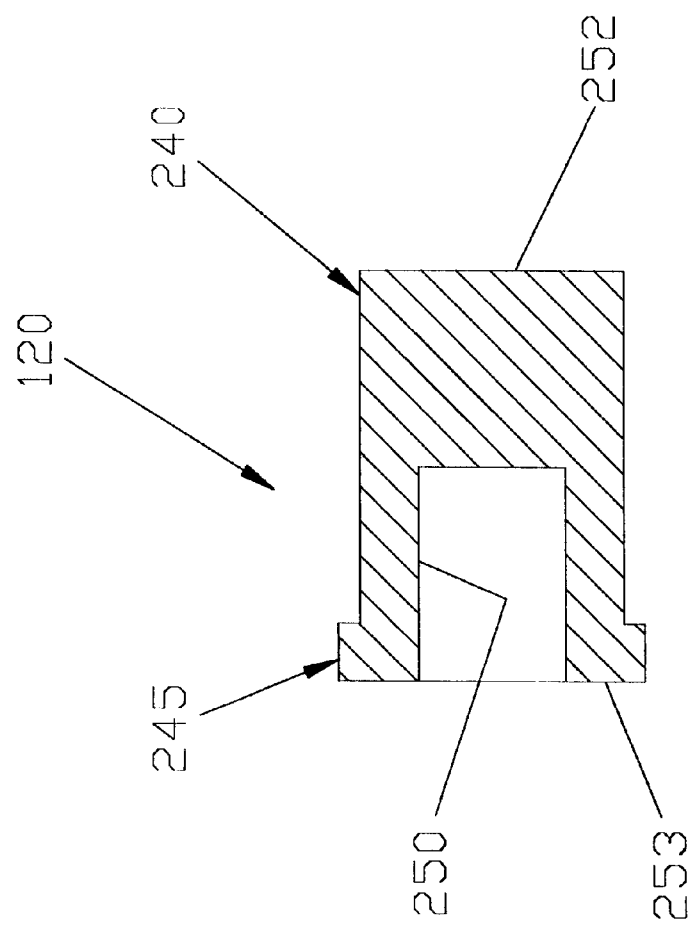
FIG. 20 is a side view in cross-section of the inserter's cap.

Referring next to FIGS. 20 and 21, cap 120 generally comprises an elastomeric material, and includes a body portion 240, an annular rim 245, and a blind hole 250. Cap 120 terminates in a distal end surface 252 and in a proximal end surface 253. Body portion 240 is generally cylindrical, and is sized and shaped to fit snugly within counterbore 155 of tubular shaft 100 (FIG. 10). Annular rim 245 projects radially outwardly from body portion 240, and is sized and shaped so as to engage proximal end surface 132 of tubular shaft 100 when the cap's body portion 240 is positioned in the shaft's counterbore 155, as will hereinafter be disclosed in further detail. Blind hole 250 opens on proximal end surface 253 and extends distally into body portion 240. Blind hole 250 provides for flexure of the proximal portion of cap 120 during assembly of cap 120 to tubular shaft 100, as will hereinafter be disclosed in further detail.

Suture anchor 5, suture 10, and inserter 15 are preferably assembled in the following manner.

First, suture 10 is drawn through bore 75 of anchor 5 and pulled back so that it lies within the anchor's two channels 80. In this position, suture 10 will extend proximally from the anchor's proximal end surface 55.

Next, tubular shaft tip 105 is assembled to tubular shaft 100. This is done by first aligning the tubular shaft tip's proximal portion 165 (FIG. 12) with the tubular shaft's distal counterbore 145 (FIG. 10). Tubular shaft tip 105 is then moved toward tubular shaft 100 so that the tubular shaft tip's cylindrical portion 165 enters the tubular shaft's counterbore 145. Tubular shaft tip 105 is advanced into counterbore 145 until the tubular shaft tip's proximal end surface 167 (FIG. 12) engages the tubular shaft's annular shoulder 147 (FIG. 10). As this occurs, proximal end surface 197 (FIG. 12) of the tubular shaft tip's distal portion 160 engages distal end surface 127 (FIG. 10) of tubular shaft 100.

Next, the free ends of suture 10 are passed through the distal portion 190 of the shaft tip's central passageway 170, through annular projection 175, and then through central passageway 135 of tubular shaft 100, until the free suture ends exit the open proximal end of the tubular shaft.

Once the free suture ends have been successfully threaded through the preceding parts, anchor 5 may be installed in the distal end of tubular shaft tip 105. More particularly, anchor 5 is oriented so that the flat sides 56 and corners 57 of the anchor's proximal portion 25 are aligned with their corresponding counterparts in distal portion 190 of the tubular shaft tip's central passageway 170. Anchor 5 is then moved toward tubular shaft tip 105 until the anchor's proximal portion 25 is fully seated within the shaft tip's distal portion 190, with the suture anchor's proximal end surface 55 resting against the tubular shaft tip's annular projection 175.

In this respect it will be understood that the relative dimensions of the anchor's proximal portion 25 and tubular shaft tip 105 will be chosen so that a driving engagement will be established between anchor 5 and tubular shaft tip 105. It will also be understood that in this configuration, the second portion 59 of the anchor's thread 30 will be engaged by and safely seated in tubular shaft tip 105, while the distal end of suture anchor 5 will project out the front of the tubular shaft tip.

Once anchor 5 has been securely positioned within distal portion 190 of tubular shaft tip 105, suture 10 may be pulled taut. Suture gripper 110 is then slid over suture 10 by passing the free ends of suture 10 through the suture gripper's internal passageway 220. Suture gripper 110 is then inserted into the proximal end of the tubular shaft's central passageway 135, and slid distally within the tubular shaft's central passageway 135 until suture gripper 110 abuts the tubular shaft tip's proximal end surface 167. By keeping suture 10 taut as suture gripper 110 engages the shaft tip's end surface 167, the suture gripper's gripping engagement with suture 10 will help keep anchor 5 mounted to tubular shaft tip 105.

The free ends of suture 10 are then passed through central passageway 235 of suture sleeve 115. Suture sleeve 115 is then inserted into tubular shaft 100. Suture sleeve 115 is slid distally along the tubular shaft's central passageway 135 until the suture sleeve's distal end surface 230 (FIG. 18) engages the suture gripper's proximal end surface 227 (FIG. 16). The free ends of suture 10 are then inserted into the annular gap formed between the outer surface of suture sleeve 115 and the inner surface of tubular shaft 100 (FIG. 1).

Tubular shaft 100 is then closed off by inserting cap 120 into the tubular shaft's open proximal end. More particularly, the cap's body portion 240 is aligned with the proximal end of tubular shaft 100. Cap 120 is then moved toward tubular shaft 100 until the cap's distal end surface 252 (FIG. 20) engages the tubular shaft's internal shoulder 157 (FIG. 10). As this occurs, the cap's annular rim 245 engages the tubular shaft's proximal end surface 132, thus sealing central passageway 135 of tubular shaft 100.

Looking next at FIGS. 22–24, suture anchor 5 is intended to be installed in a target bone 324 as follows.

Suture anchor assembly 1 is first assembled to rotary means (not shown) of the sort well known in the art for turning a shaft, e.g., suture anchor assembly 1 may be attached to the chuck of a typical powered rotary drill or to a hand drill such as a T-handle inserter. Once assembled to the aforementioned rotary means, suture anchor assembly 1 is oriented so that suture anchor 5 is positioned above cortical bone layer 325, with the anchor's distal point 50 resting on top surface 326 of bone 324. Once in this position, the rotary means are actuated so that anchor 5 is caused to rotate. As this occurs, the anchor's distal point 50 penetrates the bone's top surface 326 until flutes 35 begin to cut away a portion of cortical bone layer 325. During this operation, axial pressure is applied to the rotary means so as to cause ever increasing portions of cortical bone layer 325 to be cut away by flutes 35. In this respect it will be understood that the anchor's distal point 50 and cutting flutes 35 are configured so as to displace at least as much bone material with each rotation of the anchor as is needed to accommodate the advancing anchor.

Once distal point 50 and cutting flutes 35 have penetrated into a portion of cortical bone layer 325, thread 30 will begin to engage the hole formed by cutting flutes 35. In this way, thread 30 will tap the inner surface of the bone hole so as to allow succeeding flights of thread 30 to securely engage cortical bone layer 325.

Of course, it will be understood that anchor 5 may also be inserted into a pre-drilled hole in the cortical bone layer. More particularly, in this situation, a hole having a diameter approximately the same as minor diameter 65 (FIG. 5) of thread 30 might be pre-drilled into the target cortical bone layer. Anchor 5 may then be turned into the pre-drilled hole, thereby tapping it in the same manner as is disclosed hereinabove.

As seen in FIG. 23, as suture anchor 5 penetrates cortical bone layer 325 and cuts into cancellous bone material 328, distal end surface 162 of tubular shaft tip 105 will engage outer surface 326 of bone 324. As the rotary means continue to rotate anchor 5, thread 30 will continue to engage the tapped inner surface of the hole being formed in bone 324. Thus the rotating anchor 5 will be drawn further into target bone 324. As this happens, second portion 59 of the anchor's thread 30 begins to engage the tapped inner surface of the hole in cortical bone layer 325. More particularly, corners 57, comprising major diameter 60, engage the tapped hole in cortical bone layer 325. In this way, an additional series of flights of thread 30 (corresponding to second portion 59 of the anchor's thread 30) engage the cortical bone layer, and thereby enhance the holding power of anchor 5 in target bone 324.

As anchor 5 is drawn further into cancellous bone layer 328, the rotating anchor is pulled free from its position within the inserter's tubular shaft tip 105. As this occurs, suture 10 will pay out from the interior of inserter 15. Once anchor 5 is completely disengaged from tubular shaft tip 105, rotational driving of the anchor ceases. Inserter 15 is then withdrawn from surface 326 of bone 324 (FIG. 24). As inserter 15 is withdrawn from bone 324, additional suture 10 will pay out from the interior of inserter 15.

It should be understood that various modifications, variations and changes may be made to the above-disclosed novel suture anchor and novel inserter without departing from the scope and spirit of the present invention.

For example, and referring now to FIGS. 25–29, an alternative form of suture anchor 305 is disclosed. Suture anchor 305 is preferably substantially identical to the suture anchor 5 disclosed in detail above, except as will hereinafter be noted below or except as may be shown in the drawings. In particular, anchor 305 comprises a distal end surface 345 and distal point 350 that are formed so as to create an acute included angle with respect to longitudinal axis 318. Furthermore, no cutting flute 35 is provided with suture anchor 305.

In a further example, and referring now to FIGS. 30–35, another alternative form of suture anchor 405 is shown. Suture anchor 405 is substantially identical to the suture anchor 5 disclosed in detail above, except as will hereinafter be noted below or except as may be shown in the drawings. In particular, anchor 405 comprises a substantially blunted distal surface 445 and at least one cutting flute 450. Since suture anchor 405 lacks a sharp penetrating point, it is intended that suture anchor 405 will be deployed into a pilot hole pre-formed in the target bone.

Either of anchors 305 or 405 may be assembled to, and deployed by, the inserter 15 taught above in connection with anchor 5.

It is also anticipated that the construction of inserter 15 might be modified from that taught above without departing from the scope of the present invention. For example, with the foregoing embodiment of inserter 15, tubular shaft 100 and tubular shaft tip 105 are formed as separate and distinct members which are subsequently joined together during assembly. It is anticipated, however, that tubular shaft 100 and tubular shaft tip 105 might be formed as a single integral member, e.g., by molding or by machining the member from a single piece of material.

Still other changes may be made to the embodiments disclosed above without departing from the scope of the present invention.

What is claimed is:

1. A suture anchor comprising:

drill means disposed on a distal portion of said suture anchor for penetrating a bone when said drill means re pressed against the bone and said suture anchor is rotated, said drill means comprising a pointed distal end surface and at least one cutting flute that extends proximally from said distal end surface;

thread means extending proximally from said drill means along a remainder of a complete length of said suture anchor, for drawing said suture anchor through the bone when said suture anchor is rotated, wherein a proximal portion of said suture anchor comprises a straight-sided cross-section that terminates in a proximal end surface of said proximal portion, straight sides of said suture anchor proximal portion interrupting a proximal portion of said thread means between inside an outside diameters of said proximal portion of said thread means; and suture attachment means disposed in said proximal portion of said suture anchor for attaching a length of suture to said suture anchor, said suture attachment means comprising a bore passing completely through said proximal portion of said suture anchor from one straight side of said proximal portion to another straight side of said proximal portion.

2. A suture anchor according to claim 1 wherein said drill means, said thread means and said suture attachment means comprise a unitary construction.

3. A suture anchor according to claim 1 wherein said suture anchor is adapted to be in threaded engagement with both a cortical bone layer and a cancellous bone layer with said suture anchor is deployed in a bone.

4. A suture anchor according to claim 1 wherein said proximal portion of said suture anchor is adapted to engage at least a portion of a cortical bone layer of a bone once said suture anchor has been fully installed in that bone.

5. A suture anchor according to claim 1 wherein said proximal portion of said suture anchor comprises a cross-section adapted to transmit a torsional load.

6. A suture anchor according to claim 5 wherein said proximal portion of said suture anchor comprises a hexagonal cross-section.

7. A suture anchor according to claim 1 wherein said suture attachment means further comprise a pair of channels, each communicating between an end of said or and said proximal end surface of said suture anchor.

8. A suture anchor according to claim 7 wherein each of said channels is adapted to receive a portion of the length of suture mounted to said suture attachment means so as to: (i) prevent said thread means from cutting the length of suture during insertion of said suture anchor into the bone, and (ii) allow for sliding movement of the length of suture relative to said proximal portion of said suture anchor once said suture anchor has been installed in a bone.

9. A system for attaching suture to a bone comprising:

a suture anchor comprising:

drill means disposed on a distal portion of said suture anchor for penetrating a bone when said drill means are pressed against the bone and said suture anchor is rotated, said drill means comprising a pointed distal end surface dispose on said distal portion of said suture anchor and at least one cutting flute that extends proximally from said distal end surface;

thread means extending proximally from said drill means along a remainder of a complete length of said suture anchor, for drawing said suture anchor through the bone when said suture anchor is rotated, wherein a proximal portion of said suture anchor comprises a straight-sided cross-section that terminates in a proximal end surface of said proximal portion, straight sides of said suture anchor proximal portion interrupting a proximal portion of said thread means between inside and outside diameters of said proximal portion of said thread means; and suture attachment means disposed in said proximal portion of said suture anchor for attaching a length of suture to said suture anchor, said suture attachment means comprising a bore passing completely through said proximal portion of said suture anchor from one straight side of said proximal portion to another straight side of said proximal portion; and a suture anchor inserter comprising:
 a tubular shaft including a tubular shaft tip, wherein said tubular shaft tip comprises a straight-sided recess extending proximally into a distal end thereof, said straight-sided recess being adapted to releasably mate with said proximal portion of said suture anchor whereby said suture anchor can be driven into a bone by rotating said inserter.

10. A method for attaching a suture to bone comprising:
(a) providing:
 a suture anchor comprising:
  drill means disposed on a distal portion of said suture anchor for penetrating a bone when said drill means are pressed against the bone and said suture anchor is rotated, said drill means comprising a pointed distal end surface disposed on said distal portion of said suture anchor and at least one cutting flute that extends proximally from said distal end surface;
  thread means extending proximally from said drill means along a remainder of a complete length of said suture anchor, for drawing said suture anchor through the bone when said suture anchor is rotated, wherein a proximal portion of said suture anchor comprises a straight-sided cross-section that terminates in a proximal end surface of said proximal portion, straight sides of said suture anchor proximal portion interrupting a proximal portion of said thread means between inside and outside diameters of said proximal portion of said thread means; and
  suture attachment means disposed in said proximal portion of said suture anchor for attaching a length of suture to said suture anchor, said suture attachment means comprising a bore passing completely through said proximal portion of said suture anchor from one straight side of said proximal portion to another straight side of said proximal portion; and
 a suture anchor inserter comprising:
  a tubular shaft including a tubular shaft tip, wherein said tubular shaft tip comprises a straight-sided recess extending proximally into a distal end thereof, said straight-sided recess being adapted to releasably mate with said proximal portion of said suture anchor whereby said suture anchor can be driven into a bone by turning said inserter; and
 a length of suture, said length of suture being mounted in said suture attachment means and said suture anchor proximal portion being disposed in said recess in said tubular shaft tip;
(b) positioning said distal portion of said suture anchor on the outer surface of the bone; and
(c) advancing said inserter toward said bone while rotating said suture anchor, whereby said suture anchor is deployed into said bone.

11. A suture anchor comprising a rigid elongated body;
a distal portion of said body comprising a pointed distal end and a cutting flute;
a threaded portion of said body comprising threads extending proximally from said distal portion for a remainder of a complete length of said body; and
a proximal portion of said body comprising planar side portions extending from a proximal end of said body and interrupting a proximal plurality of said threads, said planar side portions interrupting said proximal plurality of threads between inside and outside diameters of said proximal plurality of threads; and
said proximal portion of said body defining a bore extending through said body from a first of said planar side portions to a second of said planar side portions.

12. A suture anchor comprising a rigid elongated body;
threads extending proximally from a distal end of said body substantially throughout a complete length of said body
a proximal portion of said body comprising planar side portions extending from a proximal end of said body and interrupting a proximal plurality of said threads, said planar side portions interrupting said proximal plurality of threads between inside and outside diameters of said proximal plurality of threads; and
said proximal portion of said body defining a bore extending through said body from a first of said planar side portions to a second of said planar side portions.

13. A suture anchor comprising:
thread means extending along substantially a complete length of said suture anchor, for drawing said suture anchor into a hole formed in a target bone when said suture anchor is placed in said hole and rotated, wherein a proximal portion of said suture anchor comprises a straight-sided cross-section that terminates in a proximal end surface of said proximal portion, straight sides of said suture anchor proximal portion interrupting a proximal portion of said thread means between inside and outside diameters of said proximal portion of said thread means; and
suture attachment means disposed in said proximal portion of said suture anchor for attaching a length of suture to said suture anchor, said suture attachment means comprising a bore passing completely through said proximal portion of said suture anchor from one straight side of said proximal portion to another straight side of said proximal portion.

14. A system for attaching suture to a bone comprising:
a suture anchor comprising:
 thread means extending along substantially a complete length of said suture anchor, for drawing said suture anchor into a hole formed in a target bone when said suture anchor is placed in said hole and rotated, wherein a proximal portion of said suture anchor comprises a straight-sided cross-section that terminates in a proximal end surface of said proximal portion, straight sides of said suture anchor proximal portion interrupting a proximal portion of said thread means between inside and outside diameters of said proximal portion of said thread means; and suture attachment means disposed in said proximal portion of said suture anchor for attaching a length of suture to said suture anchor, said suture attachment means comprising a bore passing completely through said proximal portion of said suture anchor from one straight side of said proximal portion to another straight side of said proximal portion; and a suture anchor inserter comprising:
 a tubular shaft including a tubular shaft tip, wherein said tubular shaft tip comprises a straight-sided recess extending proximally into a distal end thereof, said recess being adapted to releasably mate with said proximal portion of said suture anchor whereby said suture anchor can be driven into a bone by rotating said inserter.

15. A method for attaching a suture to bone comprising:
(a) providing:
 a suture anchor comprising:
  thread means extending along substantially a complete length of said suture anchor, for drawing said suture anchor into a hole formed in a target bone when said suture anchor is placed in said hole and rotated, wherein a proximal portion of said suture anchor comprises a straight-sided cross-section that terminates in a proximal end surface of said proximal portion, straight sides of said suture anchor proximal portion interrupting a proximal portion of said thread means between inside and outside diameters of said proximal portion of said thread means; and suture attachment means disposed in said proximal portion of said suture anchor for attaching a length of suture to said suture anchor, said suture attachment means comprising a bore passing completely through said proximal portion of said suture anchor from one straight side of said proximal portion to another straight side of said proximal portion; and a suture anchor inserter comprising:
  a tubular shaft including a tubular shaft tip, wherein said tubular shaft tip comprises a straight-sided recess extending proximally into a distal end thereof, said recess being adapted to releasably mate with said proximal portion of said suture anchor whereby said suture anchor can be driven into a hone by turning said inserter; and
  a length of suture, said length of suture being mounted in said suture attachment means and said suture anchor proximal portion being disposed in said recess in said tubular shaft tip;

(b) forming the hole in the target bone;
(c) positioning a distal portion of said anchor in the hole formed in the target bone; and
(d) advancing said inserter toward said bone while rotating said anchor, whereby said anchor is deployed into said bone.

* * * * *